(12) United States Patent
Kaemmerer et al.

(10) Patent No.: US 9,498,628 B2
(45) Date of Patent: Nov. 22, 2016

(54) ELECTRODE SELECTION FOR ELECTRICAL STIMULATION THERAPY

(71) Applicant: Medtronic, Inc., Minneapolis, MN (US)

(72) Inventors: William F. Kaemmerer, Edina, MN (US); Siddharth Dani, Minneapolis, MN (US); Allison T. Connolly, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/724,327

(22) Filed: May 28, 2015

(65) Prior Publication Data

US 2016/0144186 A1 May 26, 2016

Related U.S. Application Data

(60) Provisional application No. 62/082,890, filed on Nov. 21, 2014.

(51) Int. Cl.
*A61N 1/36* (2006.01)
*A61N 1/05* (2006.01)
*A61N 1/372* (2006.01)

(52) U.S. Cl.
CPC ......... *A61N 1/36139* (2013.01); *A61N 1/0534* (2013.01); *A61N 1/36064* (2013.01); *A61N 1/36067* (2013.01); *A61N 1/36075* (2013.01); *A61N 1/36096* (2013.01); *A61N 1/36185* (2013.01); *A61N 1/37235* (2013.01)

(58) Field of Classification Search
None
See application file for complete search history.

(56) References Cited

U.S. PATENT DOCUMENTS

| 6,066,163 | A | 5/2000 | John |
| 8,078,281 | B2 | 12/2011 | Priori et al. |
| 8,364,272 | B2 | 1/2013 | Goetz |
| 8,428,733 | B2 | 4/2013 | Carlson et al. |
| 8,452,415 | B2 | 5/2013 | Goetz et al. |
| 8,538,537 | B2 | 9/2013 | Hulvershorn et al. |
| 8,588,899 | B2 | 11/2013 | Schiff |
| 8,620,420 | B2 | 12/2013 | Aksenova et al. |

(Continued)

FOREIGN PATENT DOCUMENTS

| WO | 2010044989 A2 | 4/2010 |
| WO | 2010109448 A1 | 9/2010 |
| WO | 2013123112 A1 | 8/2013 |

OTHER PUBLICATIONS

Connolly, et al., "Guiding Deep Brain Stimulation Contact Selection Using Local Field Potentials Sensed by a Chronically Implanted Device in Parkinson's Disease Patients," IEEE EMBS Conference on Neural Engineering, Apr. 22-24, 2015, pp. 840-843.

(Continued)

*Primary Examiner* — Kennedy Schaetzle
(74) *Attorney, Agent, or Firm* — Shumaker & Sieffert, P.A.

(57) ABSTRACT

In one example, a method includes selecting, by one or more processors and based on a representation of sensed electrical signals for a particular patient and a plurality of representations of sensed electrical signals for a plurality of other patients, a combination of electrodes of a plurality of combinations of one or more implantable electrodes for delivery of electrical stimulation to the particular patient.

25 Claims, 10 Drawing Sheets

(56) References Cited

U.S. PATENT DOCUMENTS

| | | | |
|---|---|---|---|
| 8,670,830 | B2 | 3/2014 | Carlson et al. |
| 8,744,597 | B2 | 6/2014 | King et al. |
| 8,774,923 | B2 | 7/2014 | Rom |
| 8,792,972 | B2 | 7/2014 | Zaidel et al. |
| 8,918,184 | B1* | 12/2014 | Torgerson .......... A61N 1/36185 607/46 |
| 2004/0158298 | A1* | 8/2004 | Gliner .................. A61N 1/0531 607/48 |
| 2005/0060007 | A1* | 3/2005 | Goetz ................ A61N 1/37252 607/48 |
| 2005/0154424 | A1 | 7/2005 | Tass et al. |
| 2006/0004422 | A1* | 1/2006 | De Ridder .......... A61N 1/0529 607/45 |
| 2006/0149337 | A1* | 7/2006 | John .................. A61N 1/36082 607/45 |
| 2007/0129770 | A1 | 6/2007 | Younis |
| 2007/0167856 | A1 | 7/2007 | McNames et al. |
| 2007/0265489 | A1 | 11/2007 | Fowler et al. |
| 2009/0118787 | A1* | 5/2009 | Moffitt ................ A61N 1/0534 607/45 |
| 2010/0036468 | A1 | 2/2010 | Decre et al. |
| 2010/0280334 | A1 | 11/2010 | Carlson et al. |
| 2010/0280574 | A1 | 11/2010 | Carlson et al. |
| 2011/0160796 | A1 | 6/2011 | Lane et al. |
| 2011/0184489 | A1 | 7/2011 | Nicolelis et al. |
| 2011/0224752 | A1 | 9/2011 | Rolston et al. |
| 2011/0264165 | A1 | 10/2011 | Molnar et al. |
| 2012/0053659 | A1 | 3/2012 | Molnar et al. |
| 2012/0101552 | A1 | 4/2012 | Lazarewicz et al. |
| 2013/0030500 | A1 | 1/2013 | Toader et al. |
| 2013/0085361 | A1 | 4/2013 | Mercanzini et al. |
| 2013/0197605 | A1 | 8/2013 | Carlson et al. |
| 2013/0338728 | A1 | 12/2013 | Flynn et al. |
| 2014/0081127 | A1 | 3/2014 | Patil et al. |
| 2014/0163627 | A1 | 6/2014 | Starr et al. |

OTHER PUBLICATIONS

International Search Report and Written Opinion of International Application No. PCT/US2015/055542, mailed Dec. 23, 2015, 11 pp.

Guillen, et al., "Characterization of subcortical structures during deep brain stimulation utilizing support vector machines," IEEE, Aug. 2011, 2 pp.

Muniz, et al., "Comparison among probabilistic neural network, support vector machines and logistic regression for evaluating the effect of subthalamic stimulation in Parkinson disease on ground reaction force during gait," Elsevier, Mar. 2010, 720-726 pp.

Santaniello, et al., "Closed-loop control of deep brain stimulation: a simulation study," IEEE, Feb. 2011, 2 pp.

Volkman, et al., "Basic algorithms for the programming of deep brain stimulation in Parkinson's disease," Movement Disorders, vol. 21, No. S14, 2006 pp. S284-S289.

Buzaski, et al., "The origin of extracellular fields and currents—EEG, ECoG, LFP and spikes," Nature Reviews Neuroscience, vol. 13, No. 38, Jun. 2012, p. 407-420.

Yang, et al., "Betacoupled high frequency activity and beta-locked neuronal spiking in the subthalamic nucleus of Parkinson's disease," J. Neuroscience, vol. 34, No. 38, Sep. 17, 2014, pp. 12816-12827.

Zaidel, et al., "Subthalamic spand of β oscillations predicts deep brain stimulation efficacy for patients with Parkinson's disease," Brain p. awq144, Jun. 9, 2010, 15 pp.

Stanslaski, et al., "Design and validation of a fully implantable, chronic, closed-loop neuromodulation device with concurrent sensing and stimulation," IEEE Trans on Neur System and Rehab Eng., vol. 20, No. 4, Aug. 2012, pp. 410-421.

U.S. Appl. No. 14/195,489, filed Mar. 3, 2014, by Kaemmerer.

\* cited by examiner

Fewest LOO errors

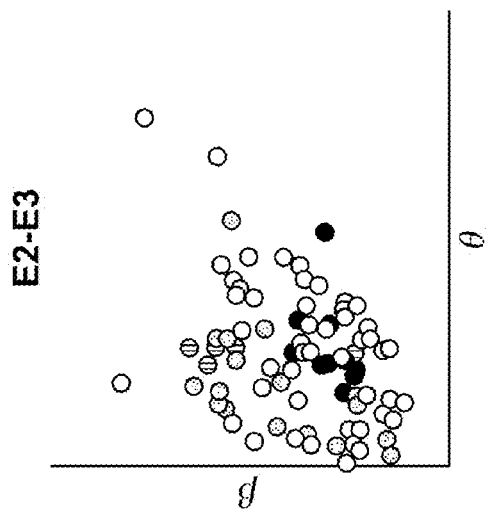
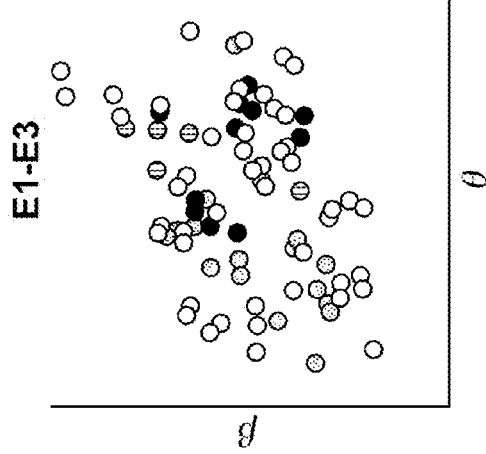
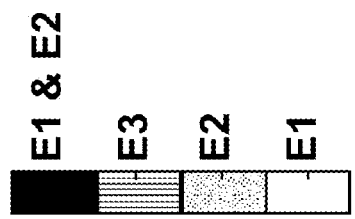
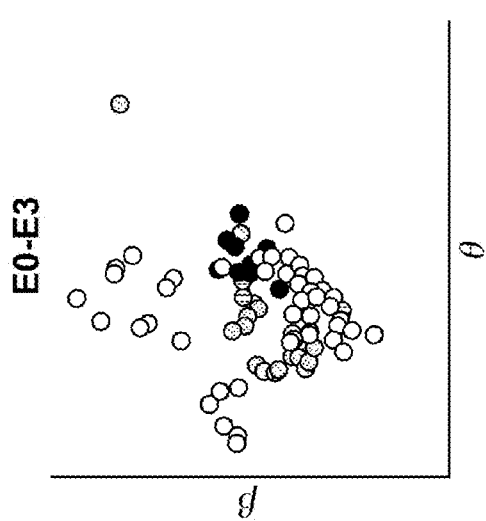

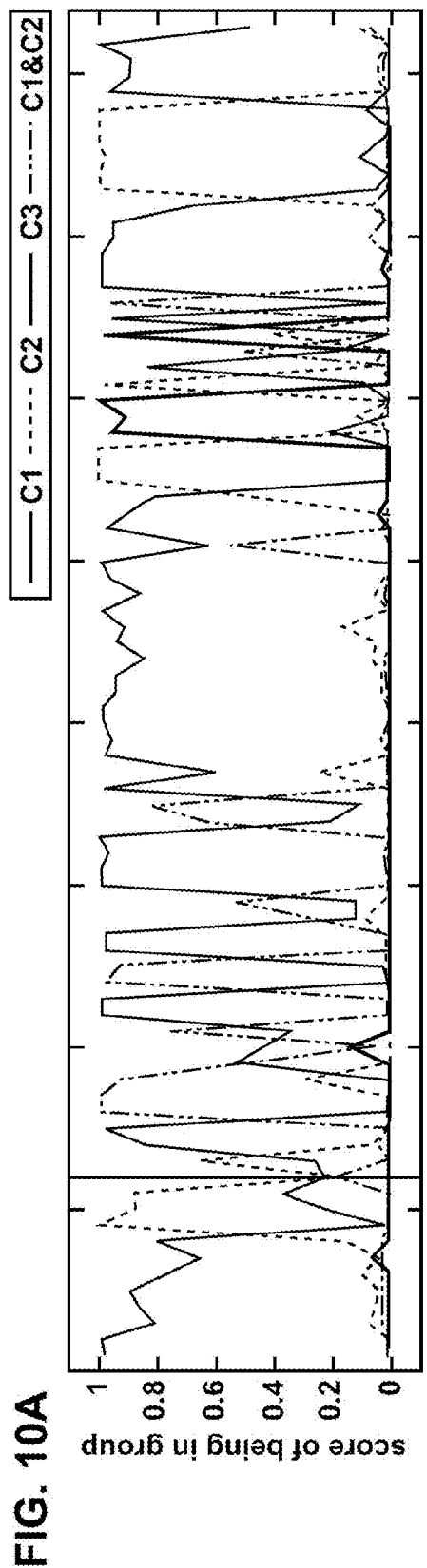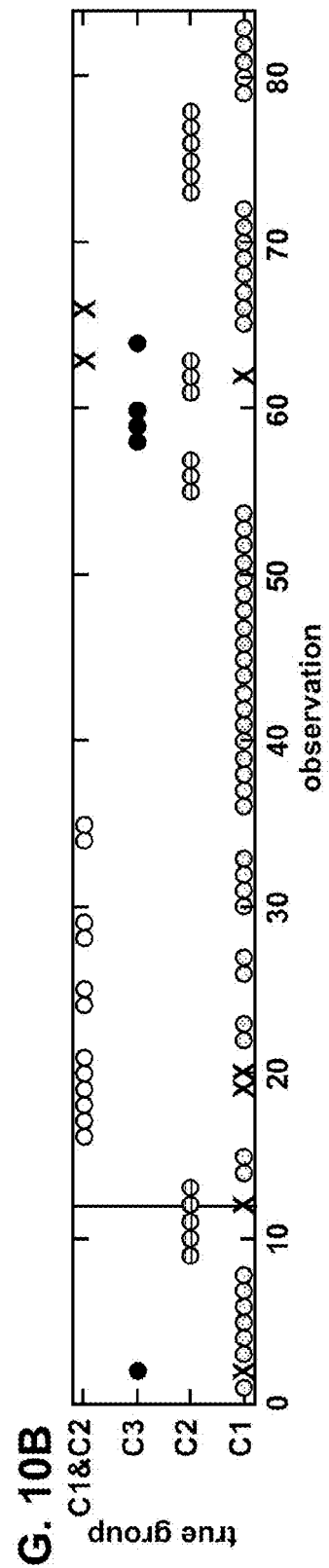
FIG. 10A
FIG. 10B

ELECTRODE SELECTION FOR ELECTRICAL STIMULATION THERAPY

This application claims the benefit of U.S. Provisional Application No. 62/082,890, filed Nov. 21, 2014, the entire content of which is incorporated by reference herein in its entirety.

TECHNICAL FIELD

The disclosure relates to electrical stimulation therapy.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agents, insulin, pain relieving agents or anti-inflammatory agents to a target tissue site within a patient. In some therapy systems, an implantable electrical stimulator delivers electrical therapy to a target tissue site within a patient with the aid of one or more electrodes, which may be deployed by medical leads and/or on a housing of the electrical stimulator, or both. In some therapy systems, therapy may be delivered via particular combinations of the electrodes carried by leads and/or by the housing of the electrical stimulator.

During a programming session, which may occur during implant of the medical device, during a trial session, or during an in-clinic or remote follow-up session after the medical device is implanted in the patient, a clinician may generate one or more therapy programs (also referred to as therapy parameter sets) that are found to provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. In examples in which electrical stimulation is delivered in the form of electrical pulses, for example, the therapy parameters may include an electrode configuration including an electrode combination and electrode polarities, an amplitude, which may be a current or voltage amplitude, a pulse width, and a pulse rate.

SUMMARY

In general, the disclosure is directed to devices, systems, and methods for selecting a combination of electrodes of one or more implantable electrodes to deliver electrical stimulation to a patient. The terms "electrode" and "contact" may be used in a substantially interchangeable manner through this disclosure. In some examples, a device may select a combination of electrodes, i.e., electrical contacts, for delivery of electrical stimulation to a particular patient based on a representation of electrical signals for the particular patient and a plurality of representations of electrical signals for a plurality of patients. In some examples, the device may use machine learning, such as support vector machines (SVM) classification, to select the combination of contacts. For instance, the device may use SVMs trained based on one or more of the plurality of representations of electrical signals for the plurality of patients. In some examples, the device may use forms of machine learning (i.e., other than SVMs). For instance, the device may use any kind of supervised or unsupervised form of machine learning to select the combination of contacts.

The contacts may be deployed on one or more implantable leads and/or a housing of an implantable stimulator. The device that uses machine learning to select the contacts may be an implantable stimulator or an external programmer for an implantable stimulator. Alternatively, the machine learning functionality may be provided in both an implantable stimulator and an external programmer for the implantable stimulator. In other examples, the implantable leads carrying the contacts may be coupled percutaneously to an external stimulator. In the case, the external stimulator includes the machine learning functionality for selection of the contacts for delivery of stimulation to the patient.

As one example, a method for controlling delivery of electrical stimulation therapy includes selecting, by one or more processors and based on a representation of sensed electrical signals for a particular patient and a plurality of representations of sensed electrical signals for a plurality of other patients, a combination of electrodes of a plurality of combinations of one or more implantable electrodes for delivery of electrical stimulation therapy to the particular patient; and generating, by the one or more processors, information to control the delivery of the electrical stimulation based on the selected combination of the electrodes.

As another example, a device includes a memory configured to store a representation of sensed electrical signals for a particular patient; and one or more processors configured to: select, based on the representation of sensed electrical signals for a particular patient and a plurality of representations of sensed electrical signals for a plurality of other patients, a combination of electrodes of a plurality of combinations of one or more implantable electrodes for delivery of electrical stimulation therapy to the particular patient; and generate information to control the delivery of the electrical stimulation based on the selected combination of the electrodes.

As another example, an implantable device includes means for selecting, based on a representation of sensed electrical signals for a particular patient and a plurality of representations of sensed electrical signals for a plurality of other patients, a combination of electrodes of a plurality of combinations of one or more implantable electrodes for delivery of electrical stimulation to the particular patient; and means for delivering the electrical stimulation to the particular patient via the selected combination of electrodes.

As another example, a programmer of an implantable device includes means for selecting, based on a representation of sensed electrical signals for a particular patient and a plurality of representations of sensed electrical signals for a plurality of other patients, a combination of electrodes of a plurality of combinations of one or more implantable electrodes for delivery of electrical stimulation to the particular patient; and means for programming the implantable medical device to deliver the electrical stimulation to the particular patient via the selected combination of electrodes.

As another example, a computer-readable storage medium stores instructions that, when executed, cause one or more processors to select, based on a representation of sensed electrical signals for a particular patient and a plurality of representations of sensed electrical signals for a plurality of other patients, a combination of electrodes of a plurality of combinations of one or more implantable electrodes for delivery of electrical stimulation to the particular patient; and generate information to control the delivery of the electrical stimulation based on the selected combination of the electrodes.

As another example, a system includes one or more processors configured to select, based on a representation of sensed electrical signals for a particular patient and a plurality of representations of sensed electrical signals for a plurality of other patients, a combination of electrodes of a plurality of combinations of one or more implantable electrodes for delivery of electrical stimulation to the particular patient; and a medical device configured to deliver stimulation to the particular patient via the selected combination of electrodes.

The details of one or more examples are set forth in the accompanying drawings and the description below. Other features, objects, and advantages will be apparent from the description and drawings, and from the claims.

BRIEF DESCRIPTION OF DRAWINGS

FIGS. 9A-9C are scatterplots illustrating the $\beta$ band versus the $\beta$ band power of local field potential recorded on bipolar pairs, in accordance with one or more techniques of this disclosure.

FIG. 9D is a legend for FIGS. 9A-9C.

FIGS. 10A and 10B are graphs illustrating output of machine learning models to select a combination of contacts, in accordance with one or more techniques of this disclosure.

DETAILED DESCRIPTION

Figure 1:
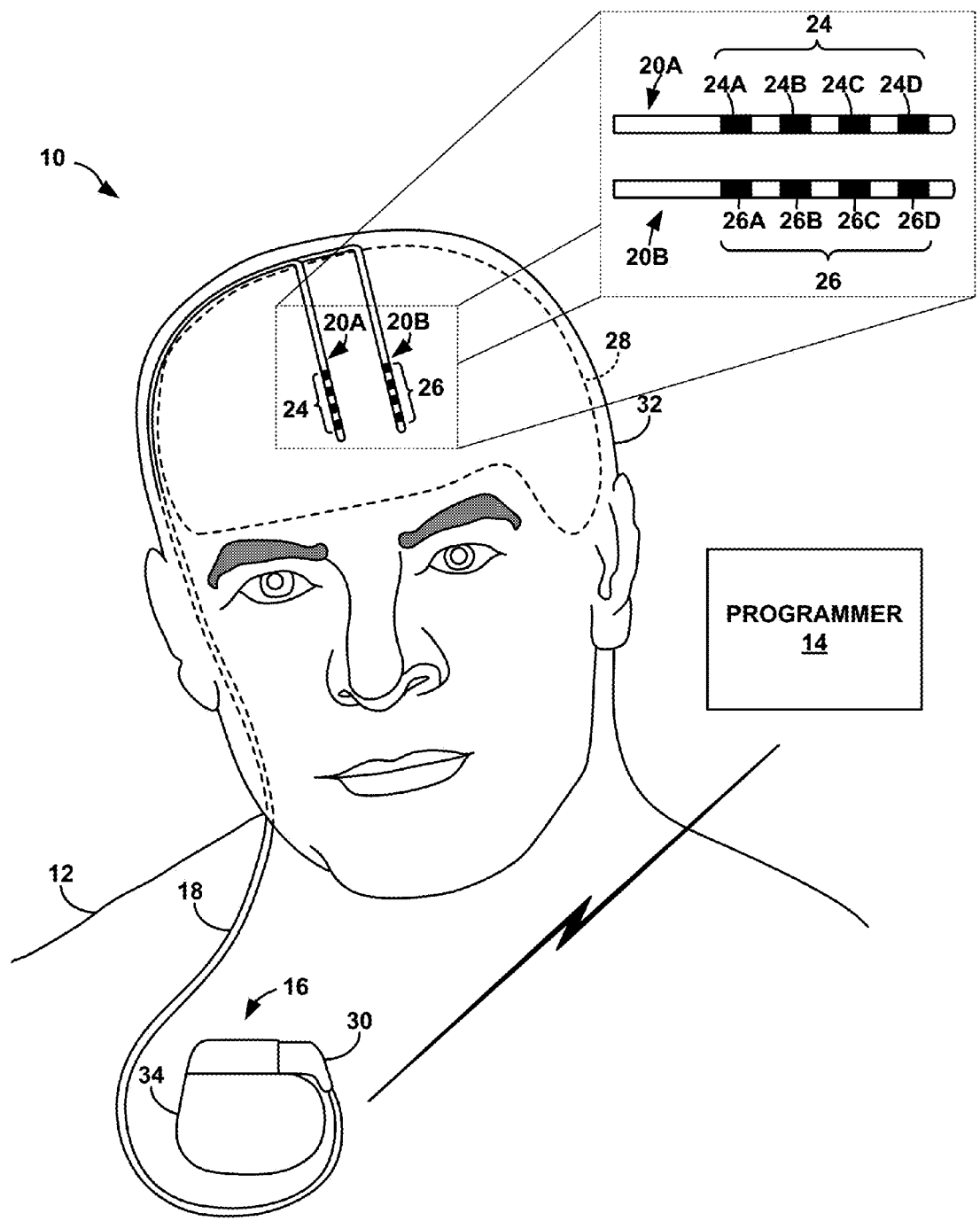
FIG. 1 is a conceptual diagram illustrating an example deep brain stimulation (DBS) system configured to deliver electrical stimulation therapy to a tissue site within a brain of a patient.

In general, the disclosure is directed to devices, systems, and methods for selecting a combination of one or more implantable electrodes to deliver electrical stimulation to a patient. For instance, a device may select a combination of electrodes for a particular patient based on a representation of electrical signals for the particular patient and a plurality of representations of electrical signals for a plurality of patients. In some examples, the device may use machine learning, such as support vector machines (SVM) classifiers, referred to in this disclosure as SVMs, to select the combination of electrodes. For instance, the device may use SVMs trained based on one or more of the plurality of representations of electrical signals for the plurality of patients.

The contacts may be deployed on one or more implantable leads and/or a housing of an implantable stimulator. The device that uses machine learning to select the electrodes may be an implantable stimulator or an external programmer for an implantable stimulator. Alternatively, the machine learning functionality may be provided in both an implantable stimulator and an external programmer for the implantable stimulator. In other examples, the implantable leads carrying the electrodes may be coupled percutaneously to an external stimulator. In the case, the external stimulator includes the machine learning functionality for selection of the electrodes for delivery of stimulation to the patient.

Parkinson's disease (PD) is a progressive neuro-degenerative disorder characterized by the depletion of dopaminergic neurons in the basal ganglia-thalamo-cortical network. Upon reaching this stage, the manifestations of the disease may include one or more of the characteristic motor dysfunctions of akinesia, bradykinesia, rigidity, and tremor. In some examples, deep brain stimulation (DBS) therapy may be used to deliver electrical stimulation to treat motor signs in medication-refractory PD patients. In some examples, DBS therapy may involve the unilateral or bilateral implantation of one or more leads into the brain to deliver electrical stimulation to target structures in the basal ganglia. Selection of effective stimulation parameters for DBS therapy can be time-consuming for both the physician (also referred to as a clinician) and the patient. As such, it may be desirable to reduce the amount of time consumed to select stimulation parameters.

In some examples, a clinician may use two knowns, the stimulation input and the behavioral output, to manually select stimulation parameters. For example, the clinician may manually select a set of stimulation parameters, and cause an implanted stimulator to stimulate the patient in accordance with the set of stimulation parameters. Based on the patient's response to the stimulation, the clinician may modify one or more of the stimulation parameters until a satisfactory response to stimulation is achieved. A satisfactory response may include a reduction in PD symptoms such as the motor dysfunctions described above in combination with no side effects or at least tolerable side effects. As stated above, the manual selection of stimulation parameters can be very time-consuming. As such, it may be desirable to reduce the amount of time consumed to select stimulation parameters.

In accordance with one or more techniques of this disclosure, a device may automatically select stimulation parameters for a patient based at least on sensed neural data for the patient. For instance, a device may compare a representation of electrical signals for a patient with one or more machine learning models to automatically select electrodes to deliver electrical stimulation to the patient. In some examples, the one or more machine learning models may be trained based on one or more of a plurality of representations of electrical signals for a plurality of patients. In this way, the device may reduce programming time and may improve patient outcomes.

To implement an automated programming algorithm based upon sensed neural data, it may be useful to find the neurophysiological correlates of both behavior and stimulation. Medtronic Neuromodulation has developed an investigational device called the Activa PC+S. In addition to delivering DBS stimulation, this chronically implantable neurostimulator is capable of sensing and recording sub-microvolt local field potentials (LFPs) from pairs of electrodes on the patient's DBS lead. For research purposes, with the approval of the appropriate institutional review boards and patients' informed consent, these devices are being implanted in PD patients at multiple centers in the United States and in Europe. As part of the research protocol, recordings of LFPs are obtained from all possible pairs of electrodes at the first post-implant programming session for the patient, and at successive follow-up visits. The LFP is believed to be the optimal signal for measuring brain state in a chronic setting because it is robust to long-term changes in electrode-tissue impedance (unlike single neuron recordings), and provides a fine enough resolution of sensing in deep structures of the brain (unlike electrocorticography) (see G. Buzsáki, C. A. Anastassiou and C. Koch, "The origin of extracellular fields and currents—EEG, ECoG, LFP and spikes," Nature Reviews Neuroscience, vol. 13, no. 6, pp. 407-20, 2012.)

From the patients implanted so far with the Activa PC+S, we selected the 15 patients with idiopathic Parkinson's disease who have DBS leads placed unilaterally or bilaterally in the subthalamic nucleus (STN). We did not pre-select the recordings based on patients' disease subtype or LFP spectral pattern. Here, we use these recordings for a preliminary investigation of whether characteristics of the recordings correlate with the electrodes selected by the attending physician for the patient's DBS therapy. In some examples, oscillatory content in the beta band (13-30 Hz) of LFPs may be correlated with location and deep brain stimulation efficacy. As such, the beta activity in LFPs sensed from the various macroelectrodes by the Activa PC+S may contain information that could help in the selection of the electrodes to be used for effective stimulation. However, in some examples, to reduce bias in the selection of features, it may be beneficial to begin with a large set of spectral features.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation generator configured to generate and deliver electrical stimulation therapy to one or more regions of brain 28 of patient 12 via one or more electrodes 24, 26 of leads 20A and 20B, respectively.

In the example shown in FIG. 1, therapy system 10 may be referred to as a deep brain stimulation (DBS) system because IMD 16 is configured to deliver electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). For example, in some examples, IMD 16 may provide cortical stimulation therapy to patient 12, e.g., by delivering electrical stimulation to one or more tissue sites in the cortex of brain 28. As another example, IMD 16 may provide vagal nerve stimulation (VNS) therapy to patient 12 by delivering electrical stimulation to one or more vagal nerve tissue sites.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post-traumatic stress disorder, dysthymic disorder, and obsessive compulsive disorder (OCD)), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12.

Therapy systems configured for treatment of other patient conditions via delivery of therapy to brain 28 or another suitable target therapy delivery site in patient 12 can also be used in accordance with the techniques disclosed herein. For example, in other applications of therapy system 10, the target therapy delivery site within patient 12 may be a location proximate to a spinal cord or sacral nerves (e.g., the S2, S3 or S4 sacral nerves) in patient 12 or any other suitable nerve, organ, muscle or muscle group in patient 12, which may be selected based on, for example, a patient condition. For example, therapy system 10 may be used to deliver electrical stimulation or a therapeutic agent to tissue proximate to a pudendal nerve, a perineal nerve or other areas of the nervous system, in which cases, leads 20 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, urinary dysfunction, fecal dysfunction, sexual dysfunction, muscle stimulation, for mitigation of other peripheral and localized pain (e.g., leg pain or back pain).

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrodes on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetically sealed housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment. Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the locus coeruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus.

As another example, in the case of Parkinson's disease, for example, leads 20 may be implanted to deliver electrical stimulation to regions within the subthalamic nucleus (STN), either unilaterally or bilaterally. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. As a further example, the electrodes may be pad electrodes, which may be carried on a paddle lead or an cylindrical lead.

As illustrated in the example of FIG. 1, the set of electrodes 24 of lead 20A may include electrodes 24A, 24B, 24C, and 24D, and the set of electrodes 26 of lead 20B may include electrodes 26A, 26B, 26C, and 26D. In some examples, each of electrodes 24 and 26 may be configured to independently deliver electrical stimulation.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs (also referred to herein as "set of stimulation parameter values"). A stimulation therapy program may define one or more electrical stimulation parameter values for therapy generated by a stimulation generator of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, a charge level of an electrical stimulation, a frequency of the electrical stimulation signal, waveform shape, on/off cycling state (e.g., if cycling is "off," stimulation is always on, and if cycling is "on," stimulation is cycled on and off) and, in the case of electrical stimulation pulses, pulse rate, pulse width, and other appropriate parameters such as duration or duty cycle. In addition, if different electrodes are available for delivery of stimulation, a therapy parameter of a therapy program may be further characterized by an electrode combination, which may define selected electrodes 24, 26 and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals or another physiological parameter of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

External medical device programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device, voice activation, or another input mechanism that allows the user to navigate through the user interface of programmer 14 and provide input. If programmer 14 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, therapeutic windows for one or more electrodes 24, 26, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. Programmer 14 may assist the clinician in the creation/identification of therapy programs by providing a system for identifying potentially beneficial therapy parameter values. For example, during a programming session, programmer 14 may automatically select a combination of electrodes for delivery to therapy to the patient. In some examples, at least some of the therapy programs may have the same electrode combination (but different values of at least one other therapy parameter) and these therapy programs may be organized into subsets, each subset having the same electrode combination. A processor of programmer 14 may select the most efficacious therapy program for each subset and display a list of the selected therapy programs. The clinician may select a therapy program from the list to provide therapy to patient 12 to address symptoms associated with the patient condition.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate with IMD 16 and, optionally, another computing device, via wireless communication. Programmer 14, for example, may communicate via wireless communication with IMD 16 using radio frequency (RF) and/or inductive telemetry techniques known in the art, which may comprise techniques for proximal, mid-range, or longer-range communication. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards, or memory sticks. Further, programmer 14 may communicate with IMD 16 and another programmer via remote telemetry techniques known in the art, communicating via a personal area network (PAN), a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

While DBS may successfully reduce symptoms of some neurological diseases, the stimulation may also cause unwanted side effects, also referred to herein as adverse effects. Side effects may include incontinence, tingling, loss of balance, paralysis, slurred speech, loss of memory, loss of inhibition, and many other neurological problems. Side effects may be mild to severe. DBS may cause one or more adverse effects by inadvertently providing electrical stimulation pulses to anatomical regions near the targeted anatomical region. These anatomical regions may be referred to as regions associated with adverse stimulation effects. For this reason, a clinician may program IMD 16 with a therapy program (or a plurality of therapy programs) that defines stimulation parameter values that balance effective therapy and minimize side effects.

With the aid of programmer 14 or another computing device, a clinician may select values for therapy parameters for therapy system 10, including an electrode combination. By selecting particular electrodes 24, 26 for delivering electrical stimulation therapy to patient 12, a clinician may modify the electrical stimulation therapy to target one or more particular regions of tissue (e.g., specific anatomical structures) within brain 28 and avoid other regions of tissue within brain 28. In addition, by selecting values for the other stimulation parameter values that define the electrical stimulation signal, e.g., the amplitude, pulse width, and pulse rate, the clinician may generate an efficacious therapy for patient 12 that is delivered via the selected electrode subset. Due to physiological diversity, condition differences, and inaccuracies in lead placement, the parameter values may vary between patients.

During a programming session, the clinician may determine one or more therapy programs that may provide effective therapy to patient 12. Patient 12 may provide feedback to the clinician as to the efficacy of the specific program being evaluated, which may include information regarding adverse effects of delivery of therapy according to the specific program. In some examples, the patient feedback may be used to determine a clinical rating scale score. Once the clinician has identified one or more programs that may be beneficial to patient 12, patient 12 may continue the evaluation process and determine which program best alleviates the condition of patient 12 or otherwise provides efficacious therapy to patient 12. Programmer 14 may assist the clinician in the creation/identification of therapy programs by providing a methodical system of identifying potentially beneficial therapy parameters.

In accordance with one or more techniques of this disclosure, and as discussed in further detail below, in some examples, a device (e.g., IMD 16, programmer 14, and/or another computing device) may be configured to automatically select a combination of electrodes of a plurality of combinations of electrodes to deliver electrical stimulation to a patient. For instance, IMD 16 may determine a representation of electrical signals for a particular patient based on electrical signals measured across one or more combinations of electrodes of a plurality of combinations of electrodes. As one example, IMD 16 may sense electrical signals (e.g., sub-microvolt local field potentials (LFPs)) from pairs of electrodes 24 and/or electrodes 26.

Based on the representation of electrical signals for the particular patient, the device may select a combination of electrodes of a plurality of combinations of electrodes to deliver electrical stimulation to the particular patient. For instance, IMD 16 may select a combination of electrodes 24, electrodes 26, and/or an electrode of IMD 16, such as a so-called case or can electrode, using machine learning models. In some examples, IMD 16 may use machine learning models trained in accordance with the techniques of FIG. 5. For instance, IMD 16 may use machine learning models trained based on a plurality of representations of electrical signals for a plurality of patients. In some examples, each respective representation of electrical signals of the plurality of representations of electrical signals is associated with a respective combination of electrodes of the plurality of electrodes selected for each respective patient of the plurality of patients. In some examples, the plurality of patients may not include the particular patient, and instead may be patient other than the particular patient. In some examples, the plurality of patients may include the particular patient. In this way, the techniques of this disclosure may automate the selection of electrode electrodes.

IMD 16 may be configured to deliver electrical stimulation to the particular patient via the selected combination of electrodes. As one example, where IMD 16 automatically selects the combination of electrodes, IMD 16 may self-configure to deliver electrical stimulation to the particular patient via the selected combination of electrodes. As another example, where programmer 14 selects the combination of electrodes, programmer 14 may configure IMD 16 to deliver electrical stimulation to the particular patient via the selected combination of electrodes. As yet another example, where another computing device selects the combination of electrodes, the other computing device may output an indication of the selected combination of electrodes to a clinician who may input the selected combination of electrodes to programmer 14, which may configure IMD 16 to deliver electrical stimulation to the particular patient via the selected combination of electrodes. As yet another example, the computing device may communicate the indication to programmer 14 which may configure IMD 16 to deliver electrical stimulation to the particular patient via the selected combination of electrodes.

Figure 2:
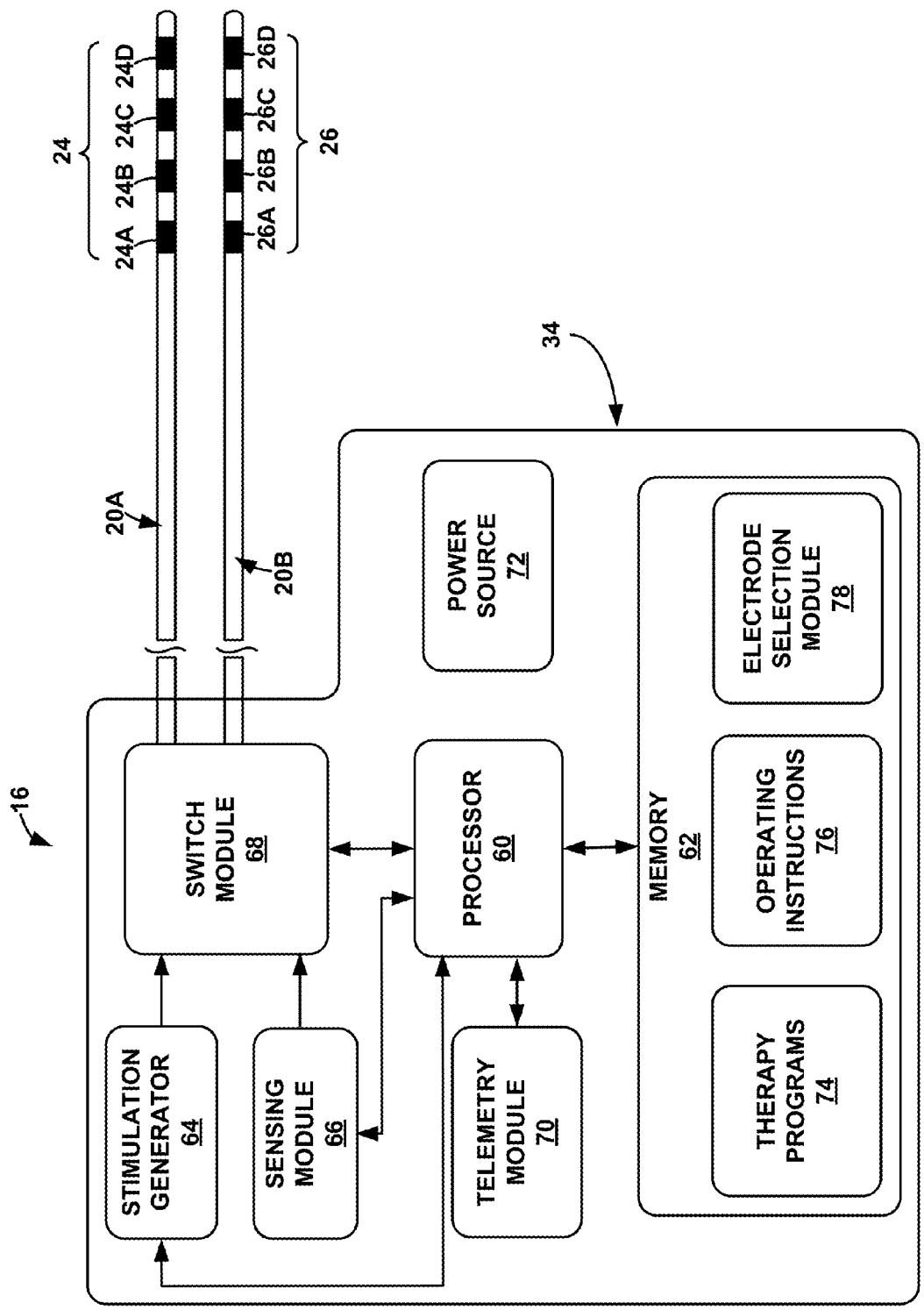
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 may store therapy programs 74, operating instructions 76, and electrode selection module 78, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. Each stored therapy program 74 may also be referred to as a set of stimulation parameter values. Operating instructions 76 guide general operation of IMD 16 under control of processor 60, and may include instructions for monitoring brain signals within one or more brain regions via electrodes 24, 26 and delivering electrical stimulation therapy to patient 12. As discussed in further detail below and in accordance with one or more techniques of this disclosure, in some examples, memory 62 may store electrode selection module 78, which may include instructions that are executable by processor 60 to select one or more electrodes to deliver electrical stimulation. For instance, electrode selection module 78 may be executable by processor 60 to select one or more of electrodes 24 and/or electrodes 26 to deliver electrical stimulation in accordance with the techniques of FIG. 4.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a selected combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more programs, such as amplitude, pulse width, and pulse rate.

In the example shown in FIG. 2, the set of electrodes 24 of lead 20A includes electrodes 24A-24D, and the set of electrodes 26 of lead 20B includes electrodes 26A-26D. Processor 60 may control switch module 68 to apply the stimulation signals generated by stimulation generator 64 to a selected combination of electrodes 24 and/or electrodes 26. In particular, switch module 68 may couple stimulation signals to selected conductors within leads 20, which, in turn, deliver the stimulation signals across selected electrodes 24 and/or electrodes 26. Switch module 68 may be a switch array, switch matrix, multiplexer, or any other type of switching module configured to selectively couple stimulation energy to selected electrodes 24 and/or electrodes 26 and to selectively sense bioelectrical brain signals with selected electrodes 24 and/or electrodes 26. Hence, stimulation generator 64 is coupled to electrodes 24 and/or electrodes 26 via switch module 68 and conductors within leads 20. In some examples, however, IMD 16 does not include switch module 68. For instance, in some examples, IMD 16 may include individual voltage or current sources coupled to each electrode (i.e., a separate voltage and/or current source for each of electrodes 24 and/or electrodes 26).

As discussed above, processor 60 may control switch module 68 to apply the stimulation signals generated by stimulation generator 64 to a selected combination of electrodes 24 and/or electrodes 26. In some examples, the selected combination of electrodes 24 and/or electrodes 26 may be unipolar. For instance, a unipolar selected combination may include one contact of either electrodes 24 or electrodes 26 in combination with an electrode on the housing of IMD 16 (i.e., case or can), where one is an anode and the other is a cathode. In some examples, the selected combination of electrodes 24 and/or electrodes 26 may be bipolar. As one example, a bipolar selected combination may include two contacts from electrodes 24, where one is an anode and the other is a cathode. As another example, a bipolar selected combination may include two electrodes from contacts 26, where one is an anode and the other is a cathode. As another example, a bipolar selected combination may include an electrode from electrodes 24 and an electrode from electrodes 26, where one is an anode and the other is a cathode. In some examples, the selected combination of electrodes 24 and/or electrodes 26 may be multipolar. As one example, a multipolar selected combination may include multiple anodes and/or multiple cathodes selected from electrodes 24. As another example, a multipolar selected combination may include multiple anodes and/or multiple cathodes selected from electrodes 26. As one example, a multipolar selected combination may include multiple anodes and/or multiple cathodes selected from electrodes 24 and electrodes 26.

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24 and/or electrodes 26 or with one or more electrodes 24 and/or electrodes 26 and at least a portion of a conductive outer housing 34 of IMD 16, an electrode on an outer housing of IMD 16 or another reference. Processor 60 may control switch module 68 to electrically connect sensing module 66 to selected electrodes 24 and/or electrodes 26. In this way, sensing module 66 may selectively sense bioelectrical brain signals with different combinations of electrodes 24 and/or electrodes 26 (and/or a reference other than an electrode of electrodes 24 and/or electrodes 26).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
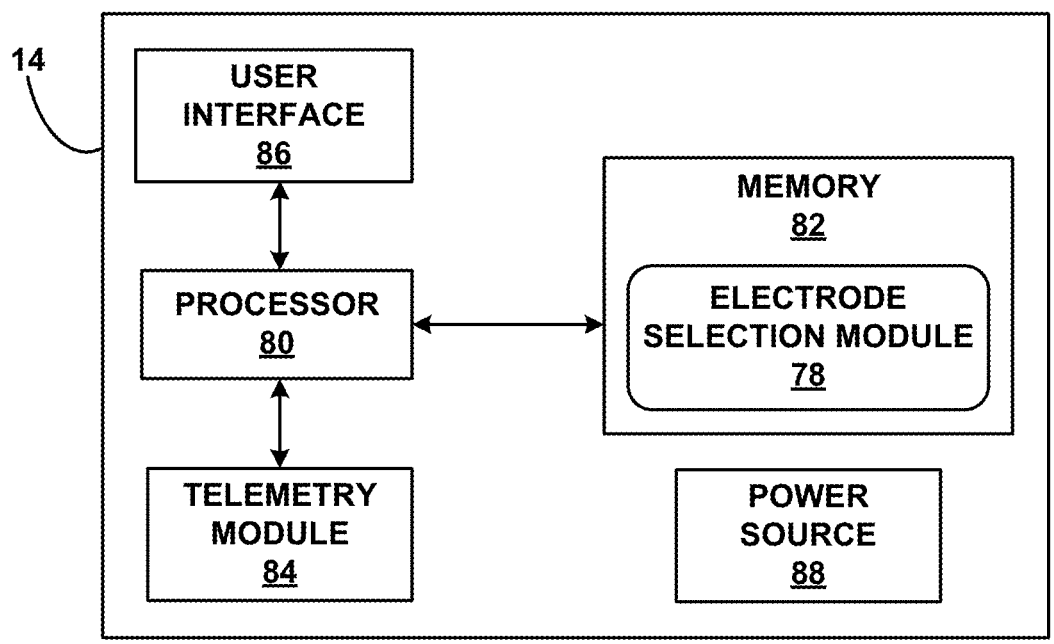
FIG. 3 is a functional block diagram illustrating components of an example medical device programmer.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, with which processor 80 may present information related to the therapy (e.g., electrodes and associated therapeutic windows). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processor 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. In the example shown in FIG. 3, memory 82 also stores electrode selection module 78.

As discussed in further detail below and in accordance with one or more techniques of this disclosure, in some examples, memory 62 may store electrode selection module 78, which may include instructions that are executable by processor 80 to select one or more electrodes, to deliver electrical stimulation. For instance, electrode selection module 78 may be executable by processor 60 to select one or more of electrodes to deliver electrical stimulation in accordance with the techniques of FIG. 4.

In some examples, patient 12, a clinician or another user may interact with user interface 86 of programmer 14 in other ways to manually select therapy programs, generate new therapy programs, modify therapy programs, transmit the new programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

While various information is illustrated and described as stored in memory 82 of programmer 14, it will be understood that some or all of this information could alternatively or additionally be stored within memory 62 of IMD 16. Moreover, at least some of the functionality ascribed to processor 80 of programmer 14 may instead or additionally be ascribed to processor 60 of IMD as discussed below (and vice versa).

Figure 4:
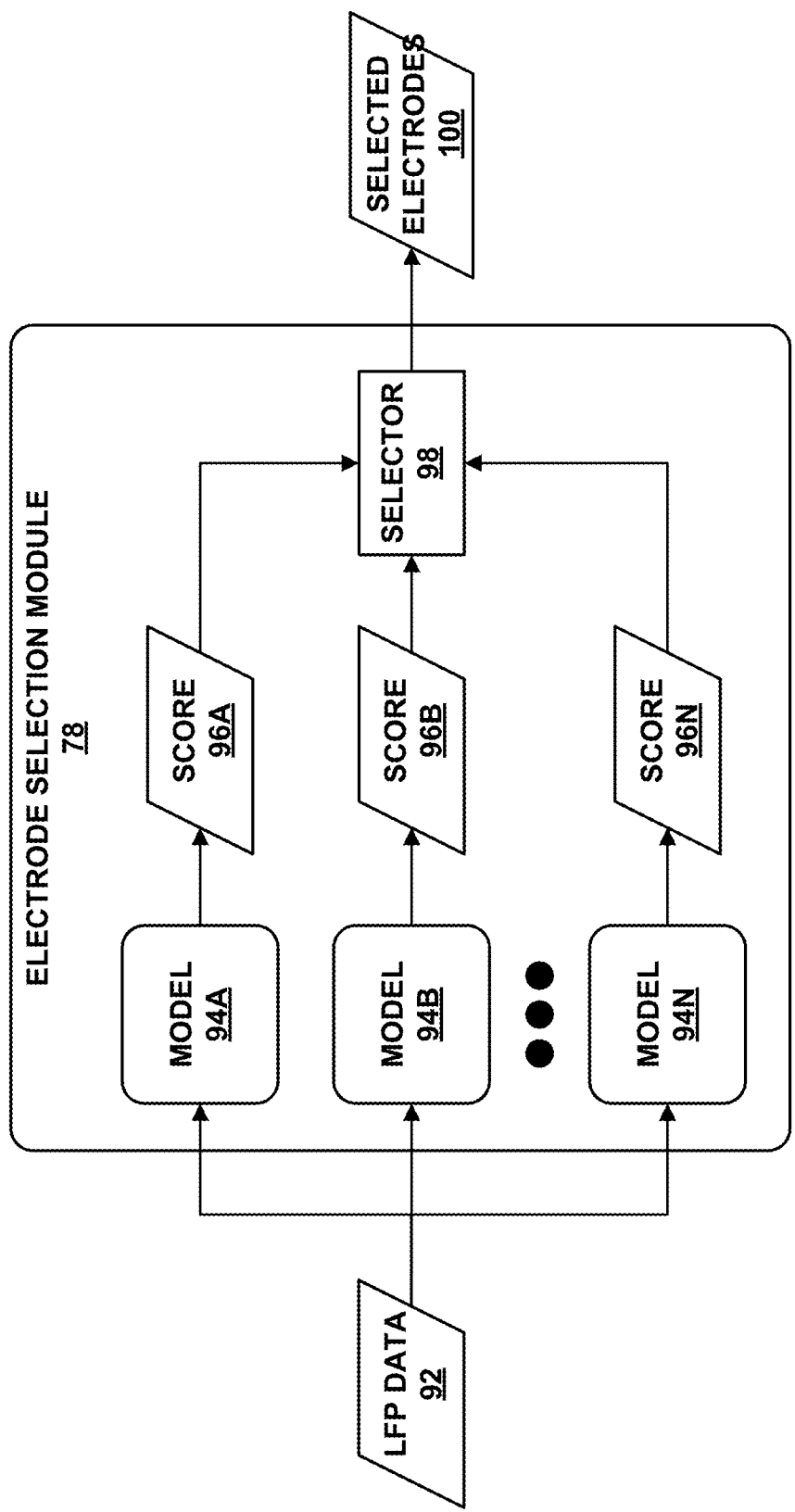
FIG. 4 is a conceptual diagram illustrating further details of one example of a contact selection module that may be provided in one or both of the devices shown in FIGS. 2 and 3, in accordance with one or more techniques of this disclosure.

FIG. 4 is a conceptual diagram illustrating further details of one example of electrode selection module 78, in accordance with one or more techniques of this disclosure. As discussed above, electrode selection module 78 may be included in either of IMD 16 or programmer 14, or any other computing device, and may include instructions for execution by one or more processors to perform electrode selection as described in this disclosure. In describing the functionality of electrode selection module 78 below, the description refers to execution of the instructions associated with the electrode selection module.

In accordance with one or more techniques of this disclosure, electrode selection module 78 may receive a representation of electrical signals for a particular patient. For instance, as illustrated in FIG. 4, contact selection module 78 may receive local field potential (LFP) data 92. In some examples, LFP data 92 may be generated by measuring LFPs across various combinations of electrode, such as electrodes 24 and/or electrodes 26 of IMD 16.

As illustrated in FIG. 4, electrode selection module 78 may include a plurality of machine learning models 94A-94N (collectively, "machine learning models 94"). In some examples, each of models 94 may be a support vector machine (SVM) classifier trained based on one or more of a plurality of representations of electrical signals for a plurality of patients. Each of machine learning models 94 may be associated with a particular combination of electrode of the plurality of electrode. For instance, machine learning model 94A may be associated with electrode 24A (i.e., machine learning model 94A may be trained based on representations of electrical signals sensed when electrode 24A was selected for unipolar stimulation), machine learning model 94B may be associated with electrode 24B (i.e., machine learning model 94B may be trained based on representations of electrical signals sensed when electrode 24B was selected for unipolar stimulation), and machine learning model 94N may be associated with both electrode 24A and electrode 24C (i.e., machine learning model 94N may be trained based on representations of electrical signals sensed when electrode 24A and electrode 24C were selected for bipolar stimulation).

Each of machine learning models 94 may be configured to determine a respective score (respectively scores 96A-96N, collectively, "scores 96") that indicates a degree to which the pattern of the electrical signals for the particular patient resembles the pattern of the electrical signals previously obtained from a plurality of patients who had in common the fact that a particular selection of electrodes for delivery of electrical stimulation yielded an effective therapy for the patient. For instance, machine learning model 94A may determine score 96A that indicates a degree to which the patient's pattern of electrical signals resembles the pattern from patients who received effective electrical stimulation therapy via electrode 24A; machine learning model 94B may determine score 96B that indicates a degree to which the patient's pattern of electrical signals resembles the pattern from patients who received effective electrical stimulation therapy via electrode 24B; machine learning model 94N may determine score 96N that indicates a degree to which the patient's pattern of electrical signals resembles the pattern from patients who received effective electrical stimulation therapy via both electrode 24A and electrode 24C in combination.

As illustrated in FIG. 4, electrode selection module 78 may include selector 98, which may be configured to select a combination of electrodes to deliver electrical stimulation to a patient. For instance, selector 98 may select a combination of electrodes based on scores 96. In some examples, the higher a score determined by a machine learning model, the more likely it is that the combination of electrodes associated with the machine learning model will be beneficial to deliver therapy to the particular patient. As one example, selector 98 may select the contact or combination of electrodes associated with the machine learning model of machine learning models 94 that determined the highest score of scores 96. For instance, where score 96A is 0.9, score 96B is 0.43, and score 96N is 0.56, selector may select the combination of electrodes associated with machine learning model 94A (i.e., contact 24A) to deliver electrical stimulation to the particular patient. As illustrated by FIG. 4, selector 98 may output the selected combination of electrodes as selected electrodes 100.

As discussed above, IMD 16 may be configured to deliver electrical stimulation to the particular patient via the selected combination of electrodes. Electrode selection module 78 may generate information to control delivery of electrical stimulation via the selected combination of electrodes. As one example, where electrode selection module 78 is included in IMD 16, electrode selection module 78 may cause IMD 16 to self-configure to deliver electrical stimulation to the particular patient via selected electrode 100. As another example, where electrode selection module 78 is included in programmer 14, electrode selection module 78 may cause programmer 14 to configure IMD 16 to deliver electrical stimulation to the particular patient via the selected combination of electrodes. As yet another example, where electrode selection module 78 is included in another computing device (i.e., not IMD 16 or programmer 14), electrode selection module 78 may cause the other computing device to output an indication of the selected combination of electrodes to a clinician who may input the selected combination of contacts to programmer 14, which may configure IMD 16 to deliver electrical stimulation to the particular patient via the selected combination of electrodes. As yet another example, electrode selection module 78 may cause the computing device to communicate the indication to programmer 14 which may configure IMD 16 to deliver electrical stimulation to the particular patient via the selected combination of electrodes.

Figure 5:
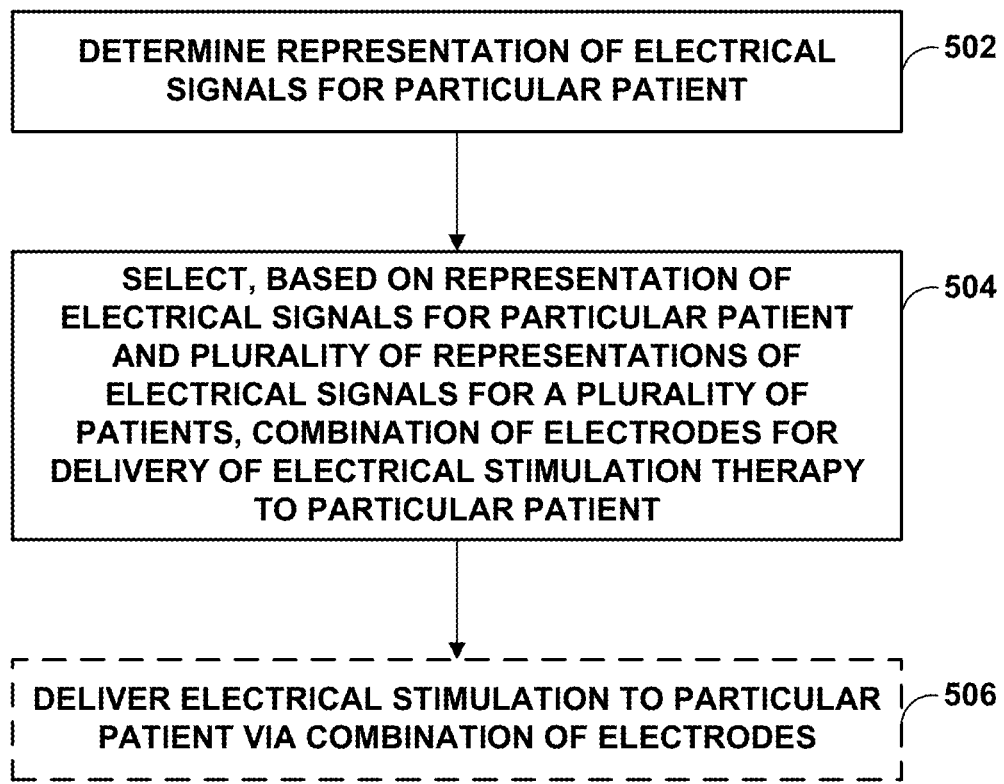
FIG. 5 is a flow diagram of an example technique for automatically selecting a combination of contacts to deliver electrical stimulation, in accordance with one or more techniques of this disclosure.

FIG. 5 is a flow diagram of an example technique for automatically selecting a combination of electrodes to deliver electrical stimulation, in accordance with one or more techniques of this disclosure. Although the technique of FIG. 5 is primarily described as being performed by processor 60 of IMD 16, in other examples, another processor, alone or in combination with processor 60, may perform any part of the technique of FIG. 5. For example, processor 80 of programmer 14 or a processor of another computing device alone or in combination with processor 80, may perform any part of the techniques of FIG. 5.

As illustrated in FIG. 5, a device, such as processor 60 of IMD 16, may determine a representation of electrical signals for a particular patient (502). As discussed above, a therapy system, such as therapy system 10, may be configured to sense bioelectrical brain signals of a patient. For instance, processor 60 may utilize one or more of electrodes 24, 26 of leads 20A and 20B, respectively, to measure a local field potential (LFP) of the particular patient's brain across varying combinations of electrodes 24 and 26. Kaemmerer, "THERAPEUTIC WINDOW DETERMINATION," U.S. application Ser. No. 14/195,489 filed Mar. 3, 2014, the entirety of which is hereby incorporated by reference, describes how electrodes may be used to both sense LFPs and deliver electrical stimulation.

Processor 60 may then select, based on the representation of electrical signals for the particular patient and a plurality of representations of electrical signals for a plurality of patients, a combination of electrodes for delivery of electrical stimulation therapy to the particular patient (504). Carlson et al., "STIMULATION ELECTRODE SELECTION," U.S. Pat. No. 8,428,733 issued Apr. 23, 2013, the entirety of which is hereby incorporated by reference, describes how a stimulation electrode combination for delivering stimulation to a patient may be selected based on bioelectrical signals sensed within a brain of the patient. In some examples, processor 60 may use one or more machine learning models to select the combination of electrodes. For instance, processor 60 may utilize a plurality of support vector machines (SVMs) that are each associated with a particular electrode or combination of electrodes of the plurality of electrodes to select the electrode or combination of electrodes for the particular patient. In some examples, each respective representation of electrical signals of the plurality of representations of electrical signals is associated with a respective electrode or combination of electrodes of the plurality of electrodes selected for each respective patient of the plurality of patients, and each of the plurality of SVMs may be trained based on one or more of the plurality of representations of electrical signals.

In some examples, each of the plurality of SVMs may be trained on signals in a theta band and/or signals in a beta band of the plurality of representations of electrical signals. In some examples, each of the plurality of SVMs may be trained based on representations of electrical signals of the plurality of representations of electrical signals that correspond to electrical signals across less than all possible combinations of electrodes. For instance, where there are twelve combinations of electrodes, each of the plurality of SVMs may be trained based on representations of electrical signals of the plurality of representations of electrical signals that correspond to electrical signals across six combinations of electrodes.

In some examples, processor 60 may be configured to use the plurality of SVMs by determining, for each respective SVM of the plurality of SVMs, a respective score that indicates a degree to which the patient's pattern of electrical signals resembles the pattern from patients who received effective electrical stimulation therapy from the respective combination of electrodes associated with the respective SVM. In some examples, the greater the degree that the representation of the electrical signals for the particular patient resembles the pattern from patients who received effective electrical stimulation therapy using the respective combination of electrodes, the greater the likelihood that delivering therapy via the respective combination of electrodes will be beneficial to the particular patient. As such, processor 60 may be configured to select, based on the scores, the combination of electrodes to deliver electrical stimulation to the particular patient.

In some examples, processor 60 may control a stimulator to deliver electrical stimulation to the particular patient via the selected combination of electrodes (506). In some examples, processor 60 may control a stimulator to refrain from delivering electrical stimulation to the particular patient via the selected combination of electrodes until receiving approval from a clinician and/or the particular patient. In some examples, processor 60 may begin delivering electrical stimulation to the particular patient via the selected combination of electrodes without receiving approval from a clinician and/or the particular patient.

In some examples, processor 60 may periodically perform the techniques of FIG. 5. For instance, processor 60 may periodically (e.g., hourly, daily, weekly, monthly, etc.) determine an updated representation of electrical signals for the particular patient, select an updated combination of electrodes based on the updated representation of electrical signals, and deliver electrical stimulation to the particular patient via the updated combination of electrodes. In this way, techniques of this disclosure may enable processor 60 to automatically adapt to changes in the particular patient's brain over time.

For example, at a first time, processor 60 may determine a representation of electrical signals for the particular patient, select a combination of electrodes based on the representation of electrical signals, and deliver electrical stimulation to the particular patient via the combination of electrodes. At a second, later, time, processor 60 may determine an updated representation of electrical signals for the particular patient, select an updated combination of electrodes based on the updated representation of electrical signals, and deliver electrical stimulation to the particular patient via the updated combination of electrodes. In some examples, such as where the particular patient's brain has not changed between the first and the second time, the updated combination of electrodes may be the same as the combination of electrodes selected based on the representation of electrical signals determined at the first time. In some examples, such as where the particular patient's brain has changed between the first and the second time, the updated combination of electrodes may be different than the combination of electrodes selected based on the representation of electrical signals determined at the first time.

Figure 6:
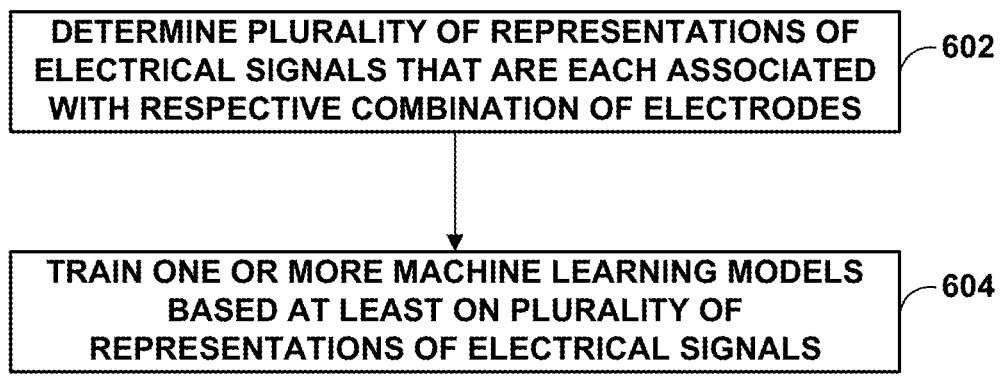
FIG. 6 is a flow diagram of an example technique for training one or more machine learning models, such as one or more SVM classifiers, in accordance with one or more techniques of this disclosure.

FIG. 6 is a flow diagram of an example technique for training one or more machine learning models, in accordance with one or more techniques of this disclosure. Although the technique of FIG. 6 is primarily described as being performed by processor 80 of programmer 14, in other examples, another processor, alone or in combination with processor 80, may perform any part of the technique of FIG. 6. For example, processor 60 of IMD 16 or a processor of another computing device alone or in combination with processor 80, may perform any part of the techniques of FIG. 6.

In some examples, a device may perform data collection and management to develop and train one or more machine learning models. For example, as illustrated in FIG. 6, a device, such as processor 80 of programmer 14, may determine a plurality of representations of electrical signals that are each associated with a respective combination of electrodes (602). A representation of electrical signals may be associated with a particular combination of electrodes where a clinician selects the particular combination of electrodes during the same session as (or temporally proximate, e.g., within 1 hour, 1, day, etc., to the time where) the representation of electrical signals is sensed. As discussed above, a therapy system, such as therapy system 10, may be configured to sense bioelectrical brain signals or another physiological parameter of a patient. An example of a therapy system which may be configured to sense bioelectrical brain signals is the Activa PC+S produced by Medtronic Inc. In some examples, a therapy system (e.g., Activa PC+S), configured to sense bioelectrical brain signals, may be implanted in a plurality of patients (e.g., with idiopathic Parkinson's disease). In each of the plurality of patients, the therapy system may be attached to DBS leads (e.g., Model 3389 produced by Medtronic Inc.) positioned in the patient's STN.

The implanted therapy systems may be used to generate the plurality of representations of electrical signals. For instance, during device implantation and follow-up sessions (e.g., extending out to six months or more), recordings may be taken/saved from the DBS leads. In some examples, the recordings may be taken with the patient at rest in the off-medication state. In some examples, a set of the recordings obtained at a single occasion may be referred to as a "montage" or a representation of electrical signals. An example montage may include 30-60 second bipolar recordings between a plurality of combinations of electrodes. For instance, where an electrode includes four electrodes (E0, E1, E2, E3), an example montage may include 30-60 bipolar recordings between the six combinations of the four electrodes (e.g., E0-E1, E0-E2, E0-E3, E1-E2, E1-E3, E2-E3), sampled at approximately 422 Hz and hardware filtered between approximately 0.5 Hz and approximately 100 Hz.

In some examples, more than one electrode may be implanted in a single patient. For example, a first electrode may be implanted in a left hemisphere of the patient's brain and a second electrode may be implanted in a right hemisphere of the patient's brain. In such examples, the electrodes may be numbered sequentially. For instance, the electrodes (C) of a first electrode may be referred to as C0, C1, C2, and C3, and the contacts of a second electrode may be referred to as C4, C5, C6, and C7. In other examples, the electrodes of a second electrode may be referred to as C8, C9, C10, and C11.

In some examples, at the end of each clinical visit, a clinician (e.g., a neurologist) may program the patient's DBS therapy by selecting, among other parameters, the stimulation electrode(s) (e.g., C0, C1, C2, C3, or some combination or two or more electrodes thereof, along with respective polarities) to provide the stimulation. As such, each of the montages (e.g., representation of electrical signals) may be associated with a respective combination of electrodes (e.g., the electrodes selected by the clinician). Table (1), below, illustrates which electrodes where selected by clinicians at clinical visits where montages were recorded for fifteen patients. As Table (1) includes more than fifteen data points, some patients had montages recorded and electrodes selected on multiple occasions. As shown by Table (1), a majority of the time, clinicians selected electrodes C1 to deliver monopolar (also referred to as unipolar) stimulation (i.e., stimulation delivered by a single anode, e.g., on a stimulator housing and a single cathode on lead, or vice versa). However, selection of electrodes C2, C3, and bipolar stimulation using both C1 and C2 were represented in the data set shown in Table (1). As discussed above, in some examples, the housing of the implanted device (e.g., outer housing 34 of IMD 16) may include one or more stimulation electrodes which may function as an anode or a cathode to deliver stimulation.

TABLE (1)

COUNTS OF PATIENTS AND MONTAGE RECORDINGS

| | SELECTED STIMULATION ELECTRODE | | | | |
|---|---|---|---|---|---|
| | C1 | C2 | C3 | C1 & C2 | TOTAL |
| No. of Leads | 17 | 6 | 2 | 3 | 28 |
| No. of Montages | 49 | 17 | 5 | 12 | 83 |

In some examples, spectral analysis may be performed to identify features which may be used to train one or more machine learning models. For instance, for each of the six recordings in a single montage, the power spectrum may be calculated using a Hamming window of length 1024 with 50% overlap, giving a frequency resolution of 0.41 Hz. The resulting power spectral density (PSD) may be used to calculate the average power in a plurality of frequency bands (e.g., 3-5 Hz, 5-10 Hz, and every 10 Hz between 10-90 Hz). In some examples, frequencies below 3 Hz may be eliminated due to baseline drift and an artifact of hardware noise centered at 2.5 Hz. The mean power in the plurality of bands (e.g., the 11 bands described above) for one or more of the recordings in a montage may be used to create a feature set for the subsequent analysis. For example, where a montage includes six recordings, one or more of the six recordings may be used to create the feature set.

Figure 7B:
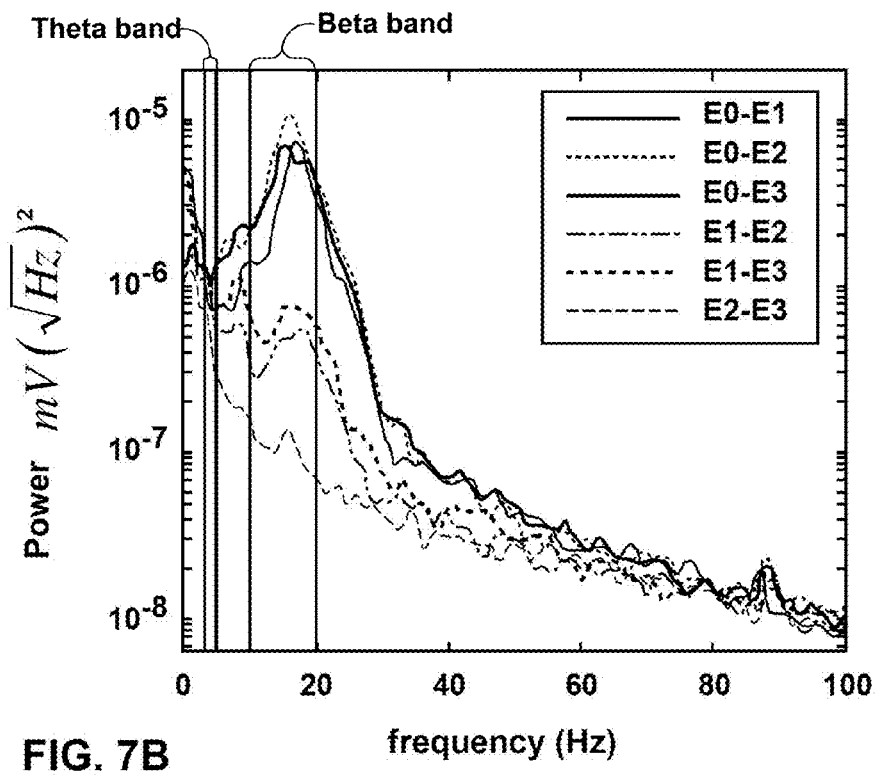
FIGS. 7A-7C illustrate examples of data that may be used to create feature sets for classification, in accordance with one or more techniques of this disclosure.
Figure 7A:
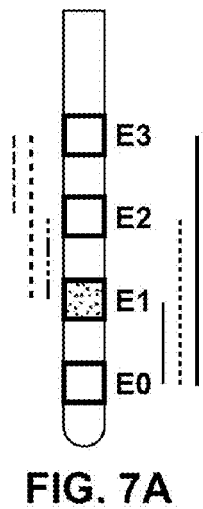
Figure 7C:
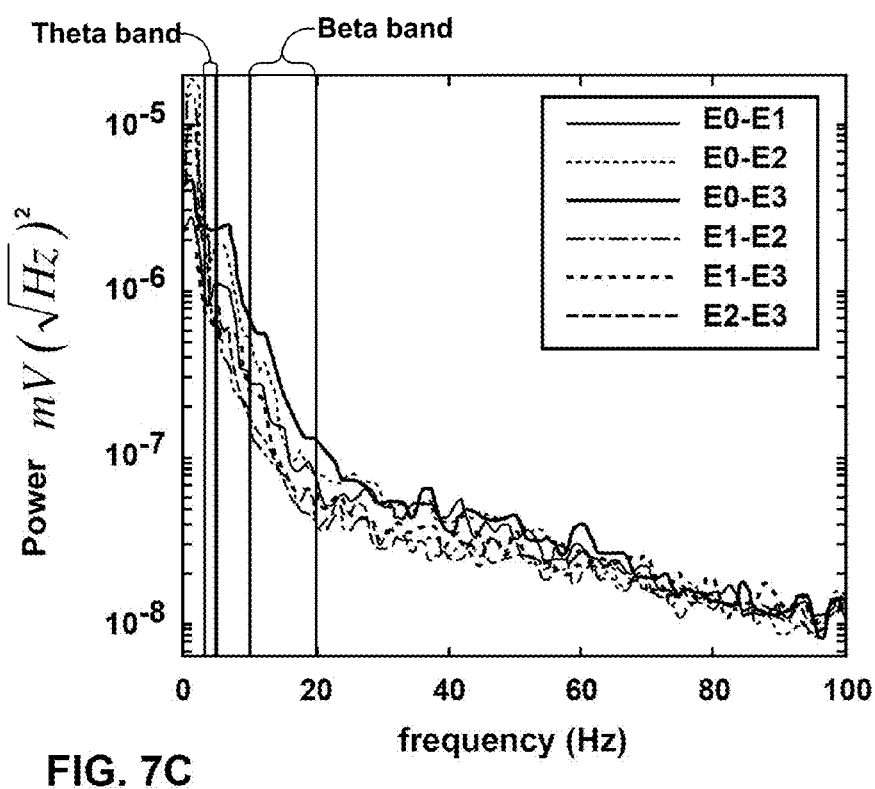

FIGS. 7A-7C illustrate some examples of data which may be used to create feature sets for classification, in accordance with one or more techniques of this disclosure. FIG. 7A is a key which indicates which electrodes are represented by the data in FIGS. 7B and 7C. Specifically, the different line types illustrated by FIG. 7A as corresponding to a combination of electrodes correspond to the different line types illustrated by FIGS. 7B and 7C. For instance, as illustrated by FIG. 7A, the thin solid line corresponds to the E0-E1 electrode combination and the thick solid line corresponds to the E0-E3 electrode combination. FIGS. 7B and 7C each include a horizontal axis representing frequency in hertz (Hz), a vertical axis representing power in the square of millivolts per root hertz $(mV/\sqrt{Hz})^2$, and a plurality of plots illustrating relationships between power and frequency for bipolar electrode pairs from example montages with (FIG. 7B) and without (FIG. 7C) a relatively high amount of beta band activity compared to activity in other frequency bands, from two different patients, both of whom had electrode E1 as their clinician-selected therapeutic. For instance, the thin solid line plot in FIGS. 7A and 7B respectively illustrates the relationship between power and frequency across electrode E0 and electrode E1 for each of the two patients. The 3-5 Hz θ band and 10-20 Hz β band are highlighted.

In some examples, several machine learning algorithms/models may be utilized to enable a device to select a combination of electrodes for a patient. Some example machine learning algorithms/models which may be used include, but are not limited to, linear discriminant analysis, k-nearest neighbors classification, classification trees, and support vector machines (SVM). Classifier performance may be evaluated based on the number of errors produced in a leave-one-out (LOO) cross-validation scheme. In some examples, the SVM method using a radial basis kernel may produce the fewest classification errors. As such, the SVM method may be utilized as the classifier. The features (power in bands and bipolar pairs) may be standardized across training observations before being used to train the classifier. SVMs can only perform binary classification. However, there is more than one potential combination of electrodes to be selected. As such, a separate SVM classifier may be trained by comparing the observations within the group (e.g., those montages associated with a particular combination of electrodes) to those not in the group (e.g., those montages not associated with the particular combination of electrodes). In order to predict the group of a new observation, the score representing the likelihood of being in the group [0,1] is calculated for each of the possible groups, and the observation is classified as being in the group with the largest score.

In some examples, using a large number of features relative to the number of observations as input to a classification problem may produce a non-generalizable result. As such, it may be desirable to identify the smallest number of features that still achieve good classification performance. In some examples, to objectively select the best features, each feature alone may be used to train a classifier, and the LOO performance may be compared. In some examples, features resulting in the worst performance may be successively eliminated until a minimum subset of features that can adequately classify the dataset remains. In some examples, the number of bipolar recording pairs may be reduced from six to three by ignoring pairs whose elimination did not degrade the classifier performance.

In some examples, visual inspection of the power spectra of all montages may not reveal an obvious way to classify them by groups corresponding to the clinically chosen stimulation electrode. In one example, training an SVM to classify montages using 10 frequency bands (3-5, 5-10, 10-20, . . . 80-90 Hz) and six recording channels (electrode pairs) yielded 6/83=7% leave-one-out cross-validation errors using a total of 60 features.

Figure 8A:
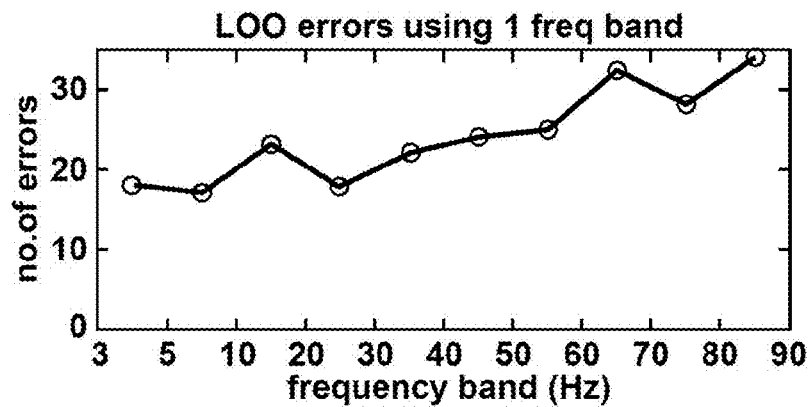
FIGS. 8A and 8B illustrate leave-one-out (LOO) classification errors, in accordance with one or more techniques of this disclosure.
Figure 8B:
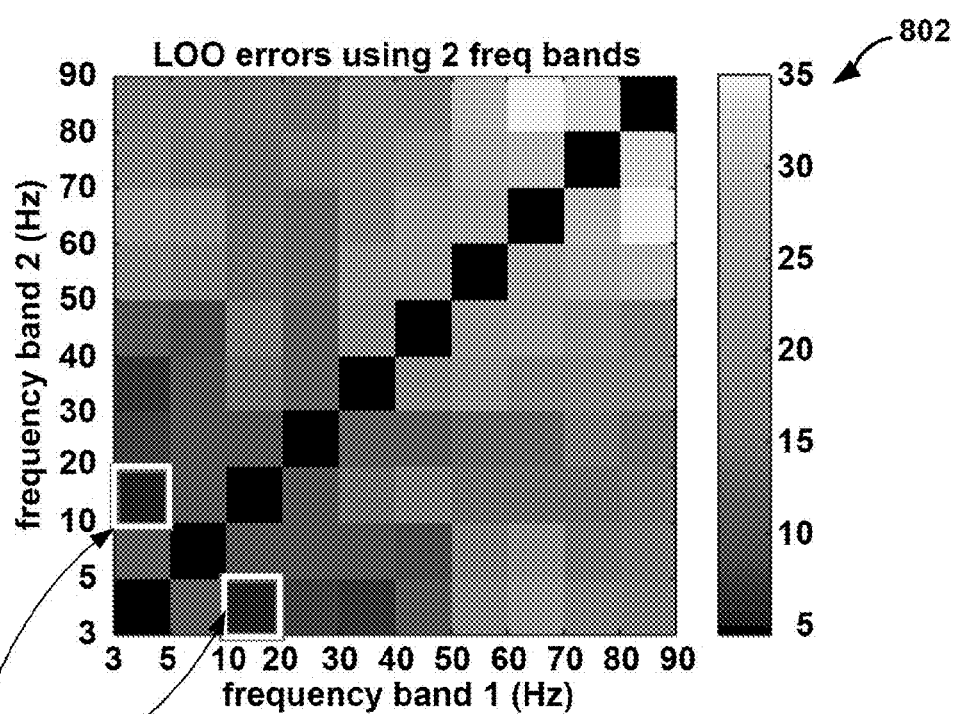

FIGS. 8A and 8B illustrate leave-one-out (LOO) classification errors, in accordance with one or more techniques of this disclosure. FIG. 8A includes a horizontal axis representing frequency bands and a vertical axis representing number of LOO errors, and a plot illustrating LOO errors using the mean power in the corresponding frequency band (on the x axis) across all six bipolar pairs. FIG. 8B includes a horizontal axis and a vertical axis that both represent frequency bands and are shaded per key 802 to illustrate LOO errors using the mean power in two frequency bands across all six bipolar pairs. In FIG. 8B, the values on the diagonal are not applicable because a band was not paired with itself; instead the LOO errors obtained for an individual band not paired with a different band is as shown in FIG. 8A.

To reduce the number of features, individual frequency bands may be compared by training classifiers using the power in that band across all recording pairs (e.g., total of six features as illustrated by FIG. 8A) to aid in determining the value (i.e., the significance) of that band for the classification purpose. In some examples, minimal LOO errors (18/83) may be produced by using the power in the 3-5 Hz θ band, whereas using just the power in 10-20 Hz β band may produce 23/83 LOO errors. Classifiers using one of the high gamma bands above 60 Hz may perform poorly (e.g., more than 28/83 errors). Classifiers may next be trained using the average power in two frequency bands across all recording pairs (e.g., total of 12 features, FIG. 8B). While the 10-20 Hz β band alone may not perform well, the combination of 3-5 Hz θ and 10-20 Hz β may produce the fewest LOO errors (5/83, white boxes illustrated in FIG. 8B). In fact, the classifier trained on this subset of frequencies may perform better than a classifier that uses all 60 features.

If there is redundant information across the recording channels, then some can be omitted and the size of the feature set may be further reduced. Following this strategy, 3-5 Hz θ and 10-20 Hz β features from three of the six bipolar pairs may be used to train classifiers. Table (2), below, illustrates example LOO errors for different frequency bands and different bipolar pairs. As illustrated in Table (2) and when using the 3-5 Hz θ band and the 10-20 Hz β band, using the three pairs referenced to E0 (E0-E1, E0-E2, E0-E3) may yield 8/83 LOO errors, the three neighboring pairs (E0-E1, E1-E2, E2-E3) may yield 15/83 LOO errors, the three pairs referenced to E3 (E0-E3, E1-E3, E2-E3) may yield the lowest errors (7/83) and the best performance using only six features.

TABLE 2

ERROR RATES USING SUBSETS OF FEATURES

| Bipolar Pairs | Leave-one-out Errors | |
| --- | --- | --- |
| | 10 Freq. Bands (3-90 Hz) | 2 Freq. Bands (θ, β) |
| E0-E1, E0-E2, E0-E3, E1-E2, E1-E3, E2-E3 | 6 | 5 |
| E0-E1, E0-E2, E0-E3 | 14 | 8 |
| E0-E1, E1-E2, E2-E3 | 10 | 15 |
| E0-E3, E1-E3, E2-E3 | 12 | 7 |

Thus, a set of six features comprised of the three bipolar pairs referenced to E3 and the two frequency bands 3-5 Hz θ and 10-20 Hz β may contain sufficient information to identify the stimulation electrode group to which a given observation belongs, in some cases with over 91% accuracy.

FIGS. 9A-9C are scatterplots illustrating the β (10-20 Hz) power vs the θ (3-5 Hz) power recorded on bipolar pairs E0-E3, E1-E3, and E2-E3 for all montages, in accordance with one or more techniques of this disclosure. FIG. 9D is a legend for FIGS. 9A-9C, in accordance with one or more techniques of this disclosure. As shown by FIG. 9D, the solid black circles in FIGS. 9A-9C correspond to recorded power when E1 and E2 were manually selected (e.g., by a clinician) to deliver electrical stimulation, the circles with vertical lines in FIGS. 9A-9C correspond to recorded power when E3 was manually selected to deliver electrical stimulation, the circles filled with dots in FIGS. 9A-9C correspond to recorded power when E2 was manually selected to deliver electrical stimulation, and the empty circles in FIGS. 9A-9C correspond to recorded power when E1 was manually selected to deliver electrical stimulation.

However, as illustrated by FIGS. 9A-9C, inspection of the data by group with respect to these features may not reveal a means of classifying the observations by visual inspection alone. As such, in some examples, it may be desirable to utilize a computational approach to, e.g., aid a practitioner in choosing a stimulation electrode for a patient. In accordance with one or more techniques of this disclosure, such a computation can consist of a collection of SVMs, each of which outputs a likelihood score that a particular choice of electrode configuration resembles that which has been made for other cases in the past (i.e., based on the training set).

Referring back now to FIG. 6 and in accordance with one or more techniques of this disclosure, the device, such as processor 80 of programmer 14, may train one or more machine learning models based at least on the plurality of representations of electrical signals (604). For instance, a plurality of SVMs that are each associated with a particular combination of electrodes may each be trained to discriminate between montages (i.e., representations of electrical signals) associated with the particular combination of electrodes (i.e., montages where a clinician selected the particular combination of electrodes) and all other montages (where a clinician did not select the particular combination of electrodes associated with this SVM).

An SVM may be considered to be associated with a particular combination of electrodes where the SVM is configured to determine a score that indicates a degree to which the pattern of sensed electrical signals from a patient resembles the pattern of sensed electrical signals previously obtained from a plurality of patients for whom delivering treatment via said particular combination of electrodes was beneficial. As one example, a particular SVM, such as machine learning model 94A of FIG. 4, may be associated with a particular combination of electrodes, such as electrode 24A. As such, the particular SVM may be trained using representations of electrical signals that are sensed during the same session when (or sensed temporally proximate to a time where) a clinician selected the particular combination of electrodes to deliver stimulation.

FIGS. 10A and 10B are graphs illustrating output of machine learning models to select an electrode or combination of electrodes, in accordance with one or more techniques of this disclosure. FIG. 10A illustrates scores generated by machine learning models (e.g., SVMs) using six features (three bipolar recordings, two frequency bands) that relate to the fit of the observation to that machine learning model's group. FIG. 10B illustrates how each observation is classified into the group whose machine learning model output the highest score. Each dot represents the clinician-selected electrode for each observation. The black X's show observations that were misclassified and the vertical location shows the incorrectly predicted-group.

In the example of FIGS. 10A and 10B, the classifier consisted of four SVMs. FIG. 10A shows the output of each SVM (the score indicating degree of resemblance to its corresponding class, Y axis) for each observation in our data set (X axis). The classifier output may be assigned as a winner-take-all to the group with the highest score. For example, observation 1 was classified correctly as group C1 because the C1 score was near 1 while the other group scores were near 0 (FIG. 10B). However, observation 12 (vertical line) was misclassified as C1 because it had the highest score of being in that group (0.226), but it was actually in group C2, which the classifier gave a score of 0.183

In some examples, power in the beta band may be used to provide some of the information used to identify the electrode chosen by the clinician for DBS therapy delivery because beta oscillations (recorded from either microelectrode or macroelectrode electrodes) may be related to the location of the active stimulation electrode independently chosen for optimal clinical outcome. However, in some examples, beta power alone may not be sufficient to identify the therapeutic stimulation electrode. As such, in some examples, the power in the theta band (3-5 Hz) may also be used to improve classifier performance. One potential explanation for this observation was that patients were not "screened" for an obvious beta peak. The value of the theta band is consistent with the report by Zaidel et al. (A. Zaidel, A. Spivak, B. Grieb, H. Bergman and Z. Israel, "Subthalamic span of β oscillations predicts deep brain stimulation efficacy for patients with Parkinson's disease," *Brain*, p. awq144, 2010) that low-frequency (3-7 Hz) power is also increased in the dorsolateral oscillatory region of the STN, and thus in their study, related to the location of the chosen active electrode. Further research may be necessary to understand if the stimulation electrode location chosen for optimal clinical effect correlates with the dorsolateral region of the STN.

In accordance with one or more techniques of this disclosure, it is be possible to develop an algorithm that uses LFP recordings from DBS leads like the Activa PC+S system to guide the identification of the electrode nearest the "physiological sweet spot" for effective DBS stimulation in the STN. Used in conjunction with post-implant brain images of lead location in the patient's STN as part of visually-guided DBS programming, or used in real-time during lead implantation or closed-loop therapy delivery, this information from brain sensing holds promise to make DBS therapy programming more efficient and effective.

While the techniques described above are primarily described as being performed by processor 60 of IMD 16 or processor 80 of programmer 14, in other examples, one or more other processors may perform any part of the techniques described herein alone or in addition to processor 60 or processor 80. Thus, reference to "a processor" may refer to "one or more processors." Likewise, "one or more processors" may refer to a single processor or multiple processors in different examples.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry.

Accordingly, the term "processor," as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples of the disclosure have been described. These and other embodiments are within the scope of the following claims.

What is claimed is:

1. A method for controlling delivery of electrical stimulation therapy, the method comprising:
   selecting, by one or more processors and based on a representation of sensed electrical signals for a particular patient and a plurality of representations of sensed electrical signals for a plurality of other patients, a combination of electrodes of a plurality of combinations of one or more implantable electrodes for delivery of electrical stimulation therapy to the particular patient; and
   generating, by the one or more processors, information to control the delivery of the electrical stimulation based on the selected combination of the electrodes.

2. The method of claim 1, wherein each respective representation of sensed electrical signals of the plurality of representations of sensed electrical signals is associated with a respective combination of electrodes of the plurality of electrodes selected for delivery of electrical stimulation for each respective patient of the plurality of patients.

3. The method of claim 2, wherein selecting the combination of electrodes comprises:
   selecting, by the one or more processors and using one or more machine learning models trained based on one or more of the plurality of representations of sensed electrical signals, the combination of electrodes for delivery of electrical stimulation to the particular patient.

4. The method of claim 3, wherein the one or more machine learning models comprise a plurality of support vector machines (SVMs) that are each associated with a particular combination of electrodes of the plurality of electrodes, and wherein selecting the combination of electrodes comprises:
   determining, for each respective SVM of the plurality of SVMs, a respective score that indicates a degree to which the representation of sensed electrical signals for the particular patient resembles that of the sensed electrical signals from a plurality of patients for whom the respective combination of electrodes that is associated with the respective SVM has been therapeutically effective for delivery of electrical stimulation; and selecting, based on the scores, the combination of electrodes to deliver electrical stimulation to the particular patient.

5. The method of claim 3, wherein the machine learning models are trained based on signals in a theta band and signals in a beta band of the plurality of representations of electrical signals, and wherein selecting the combination of electrodes comprises:
selecting, based on the signals in the theta band and the signals in the beta band of the representation of electrical signals for the particular patient, the combination of electrodes to deliver electrical stimulation to the particular patient.

6. The method of claim 3, wherein the machine learning models are trained based on signals in a theta band of the plurality of representations of electrical signals, and wherein selecting the combination of electrodes comprises:
selecting, based on the signals in the theta band of the representation of electrical signals for the particular patient, the combination of electrodes to deliver electrical stimulation to the particular patient.

7. The method of claim 3, wherein the machine learning models are trained based on signals in a beta band of the plurality of representations of electrical signals, and wherein selecting the combination of electrodes comprises:
selecting, based on the signals in the beta band of the representation of electrical signals for the particular patient, the combination of electrodes to deliver electrical stimulation to the particular patient.

8. The method of claim 5, wherein the machine learning models are trained based on fewer representations of electrical signals than all the possible representations of electrical signals from all possible combinations of electrodes of the plurality of combinations of electrodes.

9. The method of claim 3, wherein the one or more machine learning models are further trained based on one or more representations of sensed electrical signals for the particular patient and corresponding combinations of electrodes that were therapeutically effective for the particular patient.

10. The method of claim 1, wherein the one or more processors are included in a device implanted in the particular patient configured to deliver electrical stimulation to the particular patient using the one or more implantable electrodes, the method further comprising:
determining, by the one or more processors, the representation of electrical signals for the particular patient based on electrical signals measured across one or more combinations of contacts of the plurality of combinations of electrodes.

11. The method of claim 10, wherein determining the representation of electrical signals for the particular patient comprises periodically determining an updated representation of electrical signals for the particular patient, the method further comprising:
automatically selecting, by the one or more processors and based on the updated representation of electrical signals for the particular patient, an updated combination of electrodes of the plurality of combinations of electrodes for delivery of electrical stimulation; and
delivering, by the device, electrical stimulation to the particular patient via the updated combination of electrodes.

12. The method of claim 1, wherein the one or more processors are included in an external programmer of a device implanted in the particular patient, wherein generating the information to control the delivery of the electrical stimulation based on the selected combination of the electrodes comprises:
programming, by the external programmer, the device implanted in the particular patient to deliver the electrical stimulation to the particular patient via the selected combination of electrodes.

13. A device comprising:
a memory configured to store a representation of sensed electrical signals for a particular patient; and
one or more processors configured to:
select, based on the representation of sensed electrical signals for a particular patient and a plurality of representations of sensed electrical signals for a plurality of other patients, a combination of electrodes of a plurality of combinations of one or more implantable electrodes for delivery of electrical stimulation therapy to the particular patient; and
generate information to control the delivery of the electrical stimulation based on the selected combination of the electrodes.

14. The device of claim 13, wherein each respective representation of sensed electrical signals of the plurality of representations of sensed electrical signals is associated with a respective combination of electrodes of the plurality of electrodes selected for delivery of electrical stimulation for each respective patient of the plurality of patients.

15. The device of claim 14, wherein, to select the combination of electrodes, the one or more processors are configured to:
select, using one or more machine learning models trained based on one or more of the plurality of representations of sensed electrical signals, the combination of electrodes for delivery of electrical stimulation to the particular patient.

16. The device of claim 15, wherein the one or more machine learning models comprise a plurality of support vector machines (SVMs) that are each associated with a particular combination of electrodes of the plurality of electrodes, and wherein, to select the combination of electrodes, the one or more processors are configured to:
determine, for each respective SVM of the plurality of SVMs, a respective score that indicates a degree to which the representation of sensed electrical signals for the particular patient resembles that of the sensed electrical signals from a plurality of patients for whom the respective combination of electrodes that is associated with the respective SVM has been therapeutically effective for delivery of electrical stimulation; and
select, based on the scores, the combination of electrodes to deliver electrical stimulation to the particular patient.

17. The device of claim 15, wherein the machine learning models are trained based on signals in a theta band and signals in a beta band of the plurality of representations of electrical signals, and wherein, to select the combination of electrodes, the one or more processors are configured to:
select, based on the signals in the theta band and the signals in the beta band of the representation of electrical signals for the particular patient, the combination of electrodes to deliver electrical stimulation to the particular patient.

18. The device of claim 15, wherein the machine learning models are trained based on either signals in a theta band of the plurality of representations of electrical signals or signals in a beta band of the plurality of representations of electrical signals, and wherein, to select the combination of electrodes, the one or more processors are configured to:

selecting, based on either the signals in the theta band of the representation of electrical signals for the particular patient or the signals in the beta band of the representation of electrical signals for the particular patient, the combination of electrodes to deliver electrical stimulation to the particular patient.

19. The device of claim 13, wherein the one or more processors are included in a device implanted in the particular patient configured to deliver electrical stimulation to the particular patient using the one or more implantable electrodes, and wherein the one or more processors are further configured to:
determine the representation of electrical signals for the particular patient based on electrical signals measured across one or more combinations of contacts of the plurality of combinations of electrodes.

20. The device of claim 19, wherein, to determine the representation of electrical signals for the particular patient, the one or more processors are configured to periodically determine an updated representation of electrical signals for the particular patient, and wherein the one or more processors are further configured to:
automatically select, based on the updated representation of electrical signals for the particular patient, an updated combination of electrodes of the plurality of combinations of electrodes for delivery of electrical stimulation; and
deliver electrical stimulation to the particular patient via the updated combination of electrodes.

21. The device of claim 13, wherein the device is configured to program a device implanted in the particular patient, and wherein, to generate the information to control the delivery of the electrical stimulation based on the selected combination of the electrodes, the one or more processors are configured to:
program the device implanted in the particular patient to deliver the electrical stimulation to the particular patient via the selected combination of electrodes.

22. A computer-readable storage medium storing instructions that, when executed, cause one or more processors of a device to:
select, based on a representation of sensed electrical signals for a particular patient and a plurality of representations of sensed electrical signals for a plurality of other patients, a combination of electrodes of a plurality of combinations of one or more implantable electrodes for delivery of electrical stimulation to the particular patient; and
generate information to control the delivery of the electrical stimulation based on the selected combination of the electrodes.

23. The computer-readable storage medium of claim 22, wherein the device is a programmer of a device implanted in the particular patient, and wherein the instructions that cause the one or more processors to generate information to control the delivery of the electrical stimulation based on the selected combination of the electrodes, comprise instructions that cause the one or more processors to:
program the device implanted in the particular patient to deliver the electrical stimulation to the particular patient via the selected combination of electrodes.

24. The computer-readable storage medium of claim 22, wherein device is implanted in the particular patient, and wherein the instructions that cause the one or more processors to generate information to control the delivery of the electrical stimulation based on the selected combination of the electrodes, comprise instructions that cause the one or more processors to:
deliver the electrical stimulation to the particular patient via the selected combination of electrodes.

25. A system comprising:
one or more processors configured to select, based on a representation of sensed electrical signals for a particular patient and a plurality of representations of sensed electrical signals for a plurality of other patients, a combination of electrodes of a plurality of combinations of one or more implantable electrodes for delivery of electrical stimulation to the particular patient; and
a medical device configured to deliver stimulation to the particular patient via the selected combination of electrodes.

* * * * *